United States Patent [19]

Le Count

[11] Patent Number: 4,576,953

[45] Date of Patent: Mar. 18, 1986

[54] QUINOLINE DERIVATIVES

[75] Inventor: David J. Le Count, Congleton, United Kingdom

[73] Assignee: Imperial Chemical Industries PLC, London, England

[21] Appl. No.: 583,035

[22] Filed: Feb. 23, 1984

[30] Foreign Application Priority Data

Mar. 29, 1983 [GB] United Kingdom ............... 8308601

[51] Int. Cl.[4] .................. A61K 31/47; C07D 215/22
[52] U.S. Cl. ..................................... 514/312; 546/157
[58] Field of Search ........................ 546/157; 424/258

[56] References Cited

U.S. PATENT DOCUMENTS

| 1,572,768 | 2/1926 | Callsen .......................... 546/157 |
| 4,435,405 | 3/1984 | Blackburn ........................ 546/157 |

FOREIGN PATENT DOCUMENTS

| 0093521 | 9/1983 | European Pat. Off. ............ 546/157 |
| 0091198 | 12/1983 | European Pat. Off. ............ 546/157 |

OTHER PUBLICATIONS

March, "Advanced Organic Chemistry", 2nd Edition, p. 819.

Primary Examiner—Donald G. Daus
Assistant Examiner—Robert Benson
Attorney, Agent, or Firm—Cushman, Darby & Cushman

[57] ABSTRACT

Compounds of the formula:

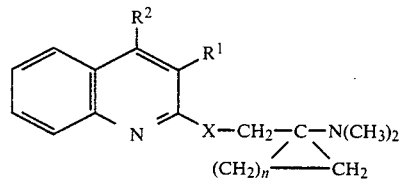

wherein X stands for an oxygen or sulphur atom, n stands for 1 or 2, $R^1$ stands for a defined (3-4C)alkyl radical, a cyclopropyl radical, or a phenyl radical which may optionally bear a halogeno, (1-4C)alkyl or (1-4C)alkoxy substituent, and $R^2$ stands for hydrogen or a (1-4C)alkyl radical, and pharmaceutically-acceptable acid-addition salts thereof. Process for the manufacture of said compounds. Pharmaceutical compositions comprising one of said compounds and a pharmaceutical diluent or carrier. The compounds are peripherally selective 5-HT antagonists.

6 Claims, No Drawings

QUINOLINE DERIVATIVES

This invention relates to quinoline derivatives which are active as 5-hydroxytryptamine antagonists.

In our European patent application No. 82302607.5 (publication No. 66993 A1) there are described and claimed quinoline derivatives of the formula:

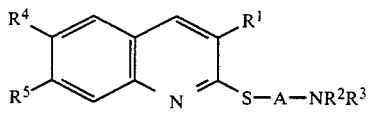

wherein:

A stands for the radical —(CH$_2$)$_2$—, which may optionally be substituted by one or two (1–2C)alkyl radicals or it may be substituted by an alkylene radical so as to form, together with the residue of the —(CH$_2$)$_2$— radical, a cycloalkylene radical of not more than 6 carbon atoms;

R$^1$ stands for an n-, iso-, or s-(3–4C)alkyl radical, or a cyclopropyl radical, or R$^1$ stands for a phenyl radical which may optionally be substituted with one or two substituents, in the latter case the same or different substituents, selected from halogen atoms and hydroxy, (1–4C)alkyl, (1–4C)alkoxy, (1–4C)alkylthio, (1–2C)perfluoroalkyl, cyano, carboxy, (1–2C)alkoxy-carbonyl, carbamoyl, N-[(1–3C)alkyl]carbamoyl and N,N-di-[(1–3C)alkyl]carbamoyl radicals, or R stands for a heteroaryl radical of five or six ring atoms containing a single hetero-atom selected from oxygen, sulphur and nitrogen atoms or containing two hetero-atoms which are either a nitrogen atom and a sulphur atom or a nitrogen atom and an oxygen atom, which heteroaryl radical may optionally be substituted with a (1–3C)alkyl radical;

R$^2$ and R$^3$, which may be the same or different, stand for hydrogen or a methyl or ethyl radical, or R$^2$ stands for a dimethylene, trimethylene or tetramethylene radical which is linked to one or other of the carbon atoms forming the two-carbon-atom backbone of the radical A so as to form, together with the adjacent nitrogen atom, a pyrrolidinyl or piperidyl radical; and one of R$^4$ and R$^5$ stands for hydrogen, and the other stands for hydrogen, a halogen atom, or a (1–3C)alkyl or (1–3C)alkoxy radical;

and pharmaceutically-acceptable acid-addition salts thereof.

The compounds are described in that patent application as being 5-hydroxytryptamine antagonists (hereinafter "5-HT antagonists"). It is disclosed that preferred compounds of that invention are 2-(2-dimethylaminoethylthio)-3-isopropylquinoline, 2-(2-dimethylaminoethylthio)-3-p-fluorophenylquinoline, 2-(2-dimethylaminoethylthio)-3-o-methoxyphenylquinoline, 2-(2-dimethylaminoethylthio)-3-p-tolylquinoline, 2-(2-dimethylamino-2-methylpropylthio)-3-phenylquinoline and 2-(2-dimethylaminopropylthio)-3-phenylquinoline, and pharmaceutically-acceptable acid-addition salts thereof, and that particularly preferred compounds are 2-(2-dimethylaminoethylthio)-3-phenylquinoline and pharmaceutically-acceptable acid-addition salts thereof.

As regards the said known compounds in which A stands for the radical —(CH$_2$)$_2$— which is substituted by an alkylene radical so as to form, together with the residue of the —(CH$_2$)$_2$— radical, a cycloalkylene radical of not more than 6 carbon atoms, the only examples disclosed are compounds in which the said cycloalkylene radical is a 1,2-cycloalkylene radical. Thus, the specific cycloalkylene radicals which are disclosed are the trans-1,2-cyclopropylene and cis- and trans-1,2-cyclohexylene radicals. We have now found that novel compounds, in which the two bonds to a cycloalkylene radical are linked to the same ring carbon atom thereof, i.e. 1,1-cycloalkylene derivatives, are 5-HT antagonists of a different type from the above-mentioned known compounds. Whereas the known compounds are both centrally and peripherally active, the compounds of this invention are significantly more active peripherally than they are centrally. That is, the compounds of this invention are peripherally selective 5-HT antagonists.

According to the invention there are provided quinoline derivatives of the formula:

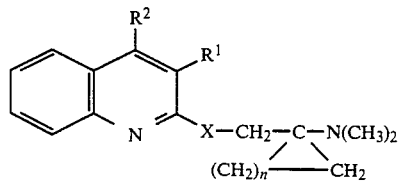

wherein:

X stands for an oxygen or sulphur atom:

n stands for 1 or 2;

R$^1$ stands for an n-, iso- or s-(3–4C)alkyl radical, or a cyclopropyl radical, or a phenyl radical which may optionally bear a halogeno, (1–4C)alkyl or (1–4C)alkoxy substituent; and R$^2$ stands for hydrogen or a (1–4C)alkyl radical:

and pharmaceutically-acceptable acid-addition salts thereof.

It will be appreciated that when n stands for 1 the cycloalkylene radical is a 1,1-cyclopropylene radical, and when n stands for 2 the cycloalkylene radical is a 1,1-cyclobutylene radical.

R$^1$ may, for example, stand for an isopropyl, s-butyl or cyclopropyl radical. Alternatively, for example, R$^1$ may stand for a phenyl radical which may optionally be substituted by a fluorine, chlorine or bromine atom, for example a p-fluorophenyl radical, or by a (1–2C)alkyl or (1–2C)alkoxy radical, for example a p-tolyl or p-methoxyphenyl radical.

R$^2$ may, for example, stand for hydrogen or a (1–2C)alkyl radical, for example a methyl radical.

Suitable salts of the invention are derived from inorganic or organic acids which provide a pharmaceutically-acceptable anion, for example hydrochloric, phosphoric, citric, benzoic, tartaric or succinic acid, or acids, for example 2-hydroxy-3-naphthoic acid or 1,1′-methylene-bis-2-hydroxy-3-naphthoic acid, which afford salts which are relatively insoluble in water and therefore have long-acting characteristics.

Preferred compounds of the invention are 2-[(1-dimethylaminocyclopropyl)methylthio]-3-phenylquinoline, 2-[(1-dimethylaminocyclopropyl)methylthio]-3-p-fluorophenylquinoline, and 2-[(1-dimethylaminocyclobutyl)methylthio]-3-phenylquinoline, and pharmaceutically-acceptable acid-addition salts thereof, for example the hydrochloride.

According to a further feature of the invention there is provided a process for the manufacture of compounds of the formula II and pharmaceutically-acceptable acid-addition salts thereof, which comprises reacting a compound of the formula:

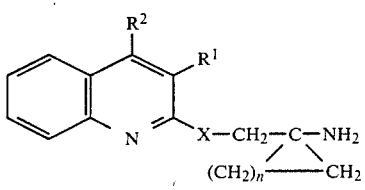
III or an acid-addition salt thereof, with (a) a borohydride having reducing properties, and formaldehyde, under acidic conditions, or (b) formaldehyde and formic acid, and wherein X, n, $R^1$ and $R^2$ have the meanings stated above.

As regards alternative (a), the borohydride may, for example, be sodium cyanoborohydride, the acidic conditions may, for example, be provided by the presence of acetic acid, and the process may be carried out in a suitable solvent, for example ethanol.

The starting materials of the formula III can be obtained by the following reaction sequence:

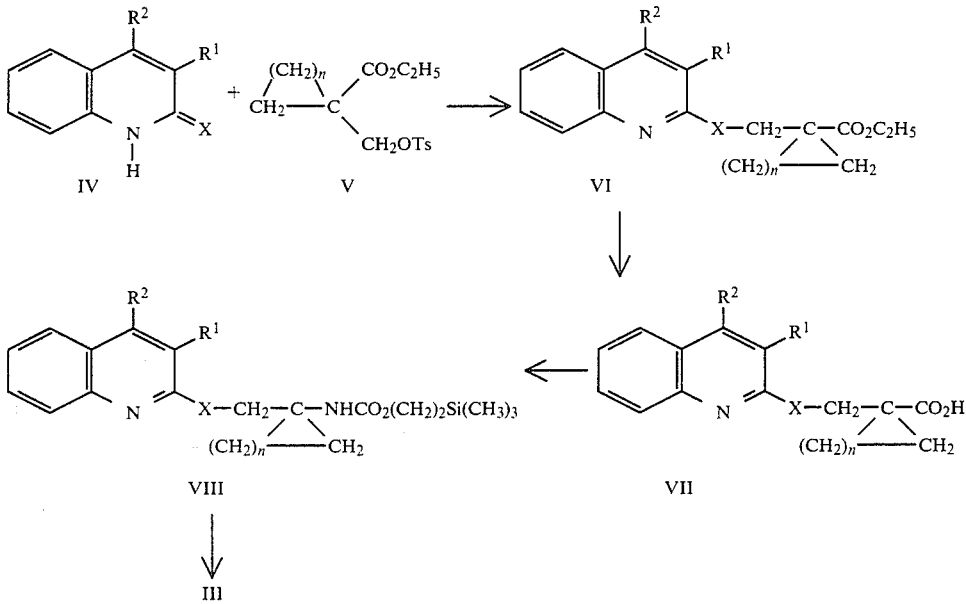
(Ts stands for the p-toluenesulphonyl radical)

The compound of the formula IV is reacted with the compound of the formula V at approximately 75° C. in the presence of sodium hydride in dimethylformamide, thus producing the ester of the formula VI. The ester is hydrolysed under alkaline conditions in conventional manner to produce the corresponding carboxylic acid of the formula VII. The remainder of the reaction sequence involves the Curtius reaction which, in essence, consists in converting the carboxylic acid (VII) successively into the corresponding azide, the corresponding transient isocyanate, a corresponding urethane derivative (VIII), and finally into the desired amine (III). The said azide may be obtained by reacting the carboxylic acid (VII) with diphenylphosphoryl azide at approximately 100° C. in the presence of triethylamine and using toluene as solvent. The resulting azide is converted into the urethane derivative (VIII) by reacting it with, for example, 2-(trimethylsilyl)ethanol in toluene at approximately 100° C. The urethane derivative (VIII) is then reacted with, for example, a source of fluoride ions, for example tetra-n-butylammonium fluoride, at approximately 60° C. in a mixture of acetonitrile and tetrahydrofuran and in an inert atmosphere, for example under argon. There is thus obtained the desired amine (III). This reaction sequence is illustrated in detail in Example 1.

The activity of compounds of the invention as 5-HT antagonists has been demonstrated in the following tests:

(1) In vitro 5-HT receptor binding (a) Binding of tritiated 5-hydroxytryptamine ($[^3H]$5-HT)

This is an in vitro test of the affinity of test compounds for the central 5-$HT_1$ receptor (Molecular Pharmacology, 1979, 16, 687). The compounds are tested for their ability to displace $[^3H]$5-HT from a receptor site on a synaptosomal preparation prepared from rat brain tissue. The compounds are tested at 3 μg./ml., and they are declared active if they produce more than 30% inhibition of specific binding. Compounds of interest are tested at a range of concentrations to establish the absolute potency for this receptor. The results are expressed as $pIC_{50}$ values, the $pIC_{50}$ being the -$log_{10}$ of the concentration of the compound needed to displace 50% of the specifically bound $[^3H]$5-HT.

(b) Binding of tritiated spiroperidol ($[^3H]$spiroperidol)

This is an in vitro test of the affinity of test compounds for the central 5-$HT_2$ receptor (Molecular Pharmacology, 1979, 16, 687). The compounds are tested for their ability to displace $[^3H]$spiroperidol from a receptor on a synaptosomal preparation prepared from rat brain cortex. The compounds are tested at 0.3, μg./ml., and they are declared active if they produce more than 30% inhibition of specific binding. Compounds of interest are tested at a range of concentrations as outlined above in respect of $[^3H]$5-HT binding. The results are expressed as $pIC_{50}$ values, the $pIC_{50}$ being the -$log_{10}$ of the concentration of the compound needed to displace 50% of the specifically bound [$^3$H]spiroperidol.

(2) Inhibition of head twitches induced in mice by 5-hydroxytryptophan (5-HTP)

This is an in vivo test of activity at central 5-HT receptors. The test involves administering a precursor of 5-HT, i.e. 5-HTP, to mice. The resultant high levels of 5-HT produced in the brain are believed to be responsible for the spontaneous twitching of the head and ears seen for a period after the administration of 5-HTP. All known centrally acting 5-HT antagonists inhibit the twitching response in a dose-dependent manner.

A range of doses of the compounds under test are administered intraperitoneally to male mice (average weight 18–20 g.; in groups of 5) 15 minutes before an intraperitoneal injection of 5-HTP at 300 mg./kg. The mice are then observed 15 minutes later for head twitches, and the results are expressed as ID$_{50}$ values. Non specific inhibition of the response due, for example, to sedation is eliminated by determining the presence or absence of the pinna reflex to tactile stimulation of the ear.

(3) Antagonism of fenfluramine-induced hyperthermia in rats

This is a sensitive in vivo test which is based on the ability of fenfluramine to release 5-HT from endogenous neuronal stores.

Female rats (Alderley Park strain; 180–220 g.) are housed (5 per cage) in a relatively warm environment (25°–28° C.) one hour prior to the beginning of the test to allow the animals to acclimatise. When the acclimatisation period is over, the rectal temperature of each animal is measured and these temperatures serve as the control reading from which all changes are calculated. For the recording of the control temperatures (−1 hour), either a test compound or the vehicle (distilled water) is administered orally or subcutaneously, and after a further hour (0 hour) the rectal temperature of each rat is measured. A dose of 15 mg./kg. of fenfluramine, or distilled water (controls), is then injected intraperitoneally. Rectal temperatures are then measured at the following times after the administration of the fenfluramine or distilled water:

30 minutes, and 1,2,3,4,5 and 6 hours

The potency of a compound in the test is expressed as an ID$_{50}$ value, i.e. the dose of the compound which reduces the hyperthermic response to a standard dose of fenfluramine by 50%.

(4) Antagonism of 5-HT-induced pressor effects in the pithed rat model

This is an in vivo test of activity at peripheral 5-HT receptors.

Female normotensive rats (Alderley Park strain; 250–300 g.) are anaesthetised using 2% halothane in oxygen, and the trachea are cannulated. The animals are then quickly pithed using the method of Gillespie and Muir (Brit. J. Pharmac. Chemother., 1967, 30, 78). After pithing, the animals are immediately respired with room air (4 cm.$^3$ at a rate of 50 cycles per min.) using a Palmer ventilation pump. The right jugular vein is cannulated for the injection of compounds. Blood pressure is recorded from the cannulated left carotid artery by means of a pressure transducer. The catheters are filled with a dilute solution of heparin in 0.9% w/v saline (the heparin solution is prepared as follows: 100,000 international units of heparin sodium are dissolved in 100 ml. of 0.9% w/v saline, and 1 ml. of the resulting solution is diluted with 199 ml. of 0.9% w/v saline). The arterial pulse is used to trigger a heart rate meter. Blood pressure and heart rate are recorded on a heated pen recorder. The animals are kept at 37° C. and monitored with a rectal thermometer. The vagi are sectioned in the neck, and before experimentation all of the animals receive atropine (1 mg./kg.) and tubocurarine (1 mg./kg.) intravenously to eliminate voluntary muscle activity.

Pressor effects to graded doses (50, 100, 250 and 500 μg.) of intravenous 5-HT are measured (these are the control values). The test compound is then administered intravenously, and 5 min. later the pressor effects to graded doses (50, 100, 250 and 500 μg.) of intravenous 5-HT are again measured. The responses to 5-HT are then measured every 15 min. in the presence of the test compound for a period of 1 hr., at which time the effect of the test compound on a sub-maximal dose (100 μg.) of 5-HT is used to calculate the ID$_{50}$ value, i.e. the dose of the test compound which causes a 50% inhibition of the 5-HT-induced pressor response. At least four doses of the test compound are used to calculate the ID$_{50}$ value, using four animals per dose level.

The potency of a specific compound of the present invention depends upon its precise chemical structure, but generally speaking the compounds of the invention exhibit the following potencies in the following ranges in the above tests:

Test (1)(a): [$^3$H]5-HT binding: pIC$_{50}$ 5–9
Test (1)(b): [$^3$H]spiroperidol binding: pIC$_{50}$ 5–9
Test (2): ID$_{50}$ 1.0–50.0 mg./kg.
Test (3): ID$_{50}$ 1.0–50.0 mg./kg.
Test (4): ID$_{50}$ less than 1.0 mg./kg.

No toxic effects or other undesirable effects have been observed with the compounds at doses at which they are active in the above-mentioned tests.

Because of their activity as peripherally selective 5-HT antagonists the compounds of the invention may be used clinically in human patients for the treatment of migraine, urticaria, asthma, hypertension, pulmonary hypertension, vascular spasm and gastrointestinal disorders, and for the inhibition of the aggregation of blood platelets. When one of the said compounds is used clinically in human patients it is recommended that it be dosed:

(a) orally at a dose of 0.5 mg./kg. to 100 mg./kg. at suitable intervals, for example three times per day,
(b) intramuscularly at a dose of 0.1 mg./kg. to 20 mg./kg. at suitable intervals,
(c) by means of a depot injection (2.5 to 100 mg./kg.), or
(d) rectally at a dose of 0.5 mg./kg. to 200 mg./kg.

According to a further feature of the invention there are provided pharmaceutical compositions comprising a compound of the formula II wherein X, n, R$^1$ and R$^2$ have the meanings stated above, or a pharmaceutically-acceptable acid-addition salt thereof, and an inert pharmaceutically-acceptable diluent or carrier.

The pharmaceutical compositions of the invention may be in a form suitable for oral, parenteral or rectal administration. Thus, for example, they may be in an orally-administrable unit dosage form, for example tablets or capsules, which may optionally be adapted for sustained release, or in an injectable form, for example a sterile injectable solution or suspension, or in the form of a suppository for rectal administration. The said pharmaceutical compositions may be produced by conventional methods using conventional diluents and carriers.

The pharmaceutical compositions of the invention may contain, in addition to a compound of the formula II, wherein X, n, $R^1$ and $R^2$ have the meanings stated above, or a pharmaceutically-acceptable acid-addition salt thereof, one or more of the following medicaments:
1. known anti-migraine agents, for example ergot alkaloids and derivatives thereof, and propranolol, clonidine, O-acetylsalicyclic acid or paracetamol;
2. known antihypertensive agents, for example α-methyldopa, α-adrenergic blocking agents, for example prazosin, β-adrenergic blocking agents, for example propranolol or atenolol, diuretics, for example hydrochlorothiazide or frusemide, and vasodilators, for example minoxidil or hydrallazine; and
3. known platelet aggregation inhibitors, for example dipyridamol, anturan, sulphinpyrazone, ticlopidine or O-acetylsalicylic acid.

The invention is illustrated but not limited by the following Examples in which the temperatures are expressed in degrees Celsius and the petroleum ether had b.p. 60°–80° unless otherwise stated:

EXAMPLE 1

Formaldehyde (37% w/w solution in water, 0.82 ml.), glacial acetic acid (0.82 ml.) and sodium cyanoborohydride (0.70 g.) were added to a solution of 2-[(1-aminocyclopropyl)methylthio]-3-phenylquinoline hydrochloride (1.2 g.) in ethanol (35 ml.). The mixture was stirred at ambient temperature for 4 hr., poured into saturated sodium bicarbonate solution (200 ml.), and extracted with ethyl acetate (3×100 ml.). The ethyl acetate extract was washed with brine (3×20 ml.), dried ($Na_2SO_4$), and evaporated in vacuo to dryness. The residual oil was chromatographed on silica gel (Merck Kieselgel 60, Art No. 9385, grain size 0.040–0.063 mm., 230–400 mesh ASTM; 180 g.) using chloroform as eluant. The relevant fraction was evaporated in vacuo to dryness, the residual oil (1.1 g.) was dissolved in methanol (20 ml.), and concentrated hydrochloric acid (0.3 ml.) was added. The resulting solution was evaporated in vacuo to dryness, and the residue was crystallised from a mixture of ethanol and diethyl ether, to yield 2-[(1-dimethylaminocyclopropyl)methylthio]-3-phenylquinoline hydrochloride, m.p. 219°.

The quinoline derivative used as starting material was obtained as follows:

3-Phenylquinolin-2-thione (5 g.) and sodium hydride (0.5 g. of a 50% w/w dispersion in mineral oil) was added to dimethylformamide (50 ml.). To the mixture was added (1-e thoxycarbonylcyclopropyl)methyl p-toluenesulphonate (6 g.). The mixture was heated at 75° for 1 hr. and kept at ambient temperature overnight. The mixture was then poured into ice-water (200 ml.), and extracted with ethyl acetate (2×100 ml.). The ethyl acetate extract was washed with brine (50 ml.), dried ($Na_2SO_4$), and evaporated in vacuo to dryness. The residue was chromatographed on silica gel (Merck Kieselgel 60; 500 g.) using 1% v/v ethyl acetate in petroleum ether to develop the column and 2% v/v ethyl acetate in petroleum ether for elution. The relevant fraction was evaporated in vacuo to dryness and the residue (5.3 g.) was dissolved in t-butanol (200 ml.). A solution of sodium hydroxide (0.80 g.) in water (8 ml.) was added. The mixture was stirred at 40° for 20 hr. More sodium hydroxide (0.20 g.) in water (2 ml.) was added, and the mixture was stirred at 55° for 5 hr. Water (50 ml.) was added, the t-butanol was evaporated in vacuo, saturated brine (50 ml.) was added, and the mixture was extracted with ethyl acetate (2×200 ml.). The ethyl acetate extract was dried ($Na_2SO_4$) and evaporated in vacuo to dryness, and to the residue was added a small volume of ethyl acetate, whereupon crystals separated. These were collected by filtration, dissolved in water (50 ml.), and the solution acidified to pH 2 with 2N- hydrochloric acid. The resulting suspension was extracted with ethyl acetate (2×50 ml.), the organic extract dried ($Na_2SO_4$) and evaporated in vacuo to dryness, and the residue crystallised from ethyl acetate and petroleum ether. There was thus obtained 2-[(1-carboxycyclopropyl)methylthio]-3-phenylquinoline, m.p. 173°.

A solution of the last-named compound (2.3 g.), diphenylphosphoryl azide (1.6 ml.) and triethylamine (1 ml.) in dry toluene (45 ml.) was heated at 100° for 4 hr. 2-(Trimethylsilyl)ethanol (1.1 ml.) was added, and the mixture was heated at 100° for 16 hr. The mixture was cooled to ambient temperature, washed with water (4×10 ml.), dried ($Na_2SO_4$), and the toluene evaporated in vacuo. The residue was crystallised from petroleum ether (b.p. 40°–60°). There was thus obtained 2-{1-[2-(trimethylsilyl) ethoxycarbonylamino]cyclopropylmethylthio}-3-phenylquinoline, m.p. 95°–97°.

The last-named compound (2 g.) was dissolved in dry acetonitrile (20 ml.), a 1 M-solution of tetra-n-butylammonium fluoride in tetrahydrofuran (10 ml.) was added, and the mixture was stirred at 60° under argon for 6 hr. The mixture was cooled, the solvent was evaporated in vacuo, and the residual oil was partitioned between ethyl acetate (50 ml.) and water (25 ml.). The mixture was separated, and the organic phase was washed with water (3×10 ml.) and then dried ($Na_2SO_4$). The solvent was evaporated in vacuo to dryness, and the residual oil was chromatographed on silica gel (Merck Kieselgel 60; 80 g.) using 1% v/v methanol in chloroform as eluant. The relevant fraction was evaporated in vacuo, the residual oil was dissolved in methanol (10 ml.), and concentrated hydrochloric acid (0.3 ml.) was added. The solution was evaporated in vacuo to dryness, and there was thus obtained 2-[(1-aminocyclopropyl)methylthio]-3-phenylquinoline hydrochloride which was sufficiently pure for use in the next stage without further purification.

EXAMPLES 2–8

In an analogous manner to that described in Example 1 there were obtained the following compounds:

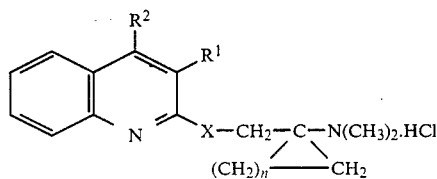

| Example No. | X | n | $R^1$ | $R^2$ | m.p. | Crystallisation solvent |
|---|---|---|---|---|---|---|
| 2 | S | 1 | $Pr^i$ | H | 170–2 | $Pr^iOH$ |
| 3 | S | 1 | p-FPh | H | 200–3 | $Pr^iOH/Et_2O$ |
| 4 | S | 1 | p-MePh | H | 196–8 | " |
| 5 | S | 1 | p-MeOPh | H | 192–4 | " |
| 6 | S | 1 | Ph | Me | 219 | $EtOH/Et_2O$ |
| 7 | O | 1 | Ph | H | 164–5 | $Pr^iOH$ |

-continued

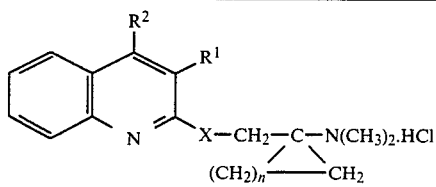

| Example No. | X | n | R¹ | R² | m.p. | Crystallisation solvent |
|---|---|---|---|---|---|---|
| 8 | S | 2 | Ph | H | 228–30 | " |

-continued

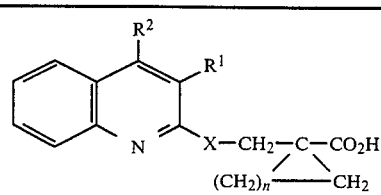

| X | n | R¹ | R² | m.p. | Crystallisation solvent |
|---|---|---|---|---|---|
| S | 2 | Ph | H | 139–41 | cyclohexane |

The following abbreviations are used in this and the following Tables:

Me methyl; Et ethyl; Pr$^i$ isopropyl; Ph phenyl.

The following compounds (which were used as starting materials or intermediates in the preparation of the above-mentioned compounds) were prepared in an analogous manner to that described in respect of the corresponding compound in Example 1 (all of the compounds described as oils were purified by medium pressure liquid chromatography, their identity was checked by nuclear magnetic resonance, and they were used as such):

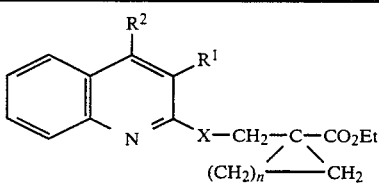

| X | n | R¹ | R² |
|---|---|---|---|
| S | 1 | Pr$^i$ | H |
| S | 1 | p-FPh | H |
| S | 1 | p-MePh | H |
| S | 1 | p-MeOPh | H |
| S | 1 | Ph | Me |
| O | 1 | Ph | H |
| S | 2 | Ph | H |

Each of these compounds was an oil. The cyclobutyl derivative used as starting material in the preparation of the compound in which n stands for 2 was made in analogous manner to that described in Bull.Soc.Chim.-France, 1965, 218 in respect of the cyclopropyl analogue.

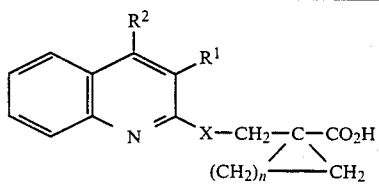

| X | n | R¹ | R² | m.p. | Crystallisation solvent |
|---|---|---|---|---|---|
| S | 1 | Pr$^i$ | H | oil | — |
| S | 1 | p-FPh | H | 161–3 | toluene/petroleum ether |
| S | 1 | p-MePh | H | 134–7 | cyclohexane |
| S | 1 | p-MeOPh | H | 130–3 | " |
| S | 1 | Ph | Me | 173 | ethyl acetate |
| O | 1 | Ph | H | 146 | " |

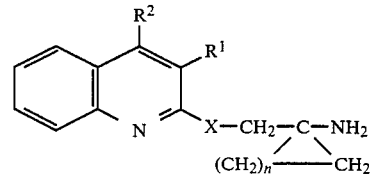

| X | n | R¹ | R² | m.p. | Crystallisation solvent |
|---|---|---|---|---|---|
| S | 1 | Pr$^i$ | H | oil | — |
| S | 1 | p-FPh | H | 128–30 | cyclohexane |
| S | 1 | p-MePh | H | 137–9 | " |
| S | 1 | p-MeOPh | H | oil | — |
| S | 1 | Ph | Me | 95–7 | petroleum ether (b.p. 40–60) |
| O | 1 | Ph | H | oil | — |
| S | 2 | Ph | H | oil | — |

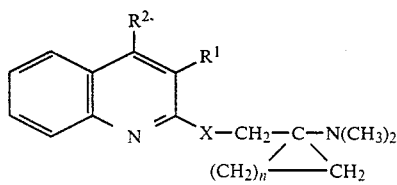

| X | n | R¹ | R² | m.p. | Crystallisation solvent |
|---|---|---|---|---|---|
| S | 1 | Pr$^i$ | H | oil | — |
| S | 1 | p-FPh | H | oil | — |
| S | 1 | p-MePh | H | oil | — |
| S | 1 | p-MeOPh | H | oil | — |
| S | 1 | Ph | Me | oil | — |
| O | 1 | Ph | H | 204 | EtOH/Et$_2$O |
| S | 2 | Ph | H | oil | — |

What we claim is:

1. A quinoline derivative of the formula:

II wherein:

X stands for an oxygen or sulphur atom;
n stands for 1 or 2;
R¹ stands for an n-, iso- or s-(3–4C)alkyl radical, or a cyclopropyl radical, or a phenyl radical which may optionally bear a halogeno, (1–4C)alkyl or (1–4C)alkoxy substituent; and R² stands for hydrogen or a (1–4C)alkyl radical;

or a pharmaceutically-acceptable acid-addition salt thereof.

2. A compound as claimed in claim 1 wherein R¹ stands for an isopropyl, s-butyl, cyclopropyl, phenyl, fluorophenyl, chlorophenyl, bromophenyl, (1–2C)alkylphenyl or (1–2C)alkoxyphenyl radical.

3. A compound as claimed in claim 1 or 2 wherein R² stands for hydrogen or a (1–2C)alkyl radical.

4. A salt as claimed in any one of claims 1 to 3 which is derived from hydrochloric, phosphoric, citric, benzoic, tartaric, succinic, 2-hydroxy-3-naphthoic or 1,1'-methylene-bis-2-hydroxy-3-naphthoic acid.

5. A compound as claimed in any one of claims 1 to 4 which is 2-[(1-dimethylaminocyclopropyl)methylthio]-3-phenylquinoline, 2-[(1-dimethylaminocyclopropyl)methylthio]-3-p-fluorophenylquinoline or 2-[(1-dimethylaminocyclobutyl)methylthio] -3-phenylquinoline, or a pharmaceutically-acceptable acid-addition salt thereof.

6. A peripherally selective 5-HT antagonist pharmaceutical composition comprising a compound of the formula II stated in claim 1, wherein X, n, R¹ and R² have the meanings stated in claim 1, or a pharmaceutically-acceptable acid-addition salt thereof, and an inert pharmaceutically-acceptable diluent or carrier.

* * * * *